(12) United States Patent
Skinner et al.

(10) Patent No.: US 10,376,196 B2
(45) Date of Patent: Aug. 13, 2019

(54) MULTI-SYMPTOM TOOLKIT FOR EVALUATING READINESS

(71) Applicant: Anthrotronix, Inc., Silver Spring, MD (US)

(72) Inventors: Anna D. Skinner, Washington, DC (US); Corinna E. Lathan, Wheaton, MD (US)

(73) Assignee: Anthrotronix, Inc., Silver Spring, MD (US)

( * ) Notice: Subject to any disclaimer, the term of this patent is extended or adjusted under 35 U.S.C. 154(b) by 175 days.

(21) Appl. No.: 15/156,205

(22) Filed: May 16, 2016

(65) Prior Publication Data

US 2016/0331293 A1 Nov. 17, 2016

Related U.S. Application Data

(60) Provisional application No. 62/161,507, filed on May 14, 2015.

(51) Int. Cl.
*A61B 5/16* (2006.01)
*A61B 5/11* (2006.01)
(Continued)

(52) U.S. Cl.
CPC .......... *A61B 5/165* (2013.01); *A61B 5/02055* (2013.01); *A61B 5/1118* (2013.01); *A61B 5/0022* (2013.01); *A61B 5/01* (2013.01); *A61B 5/024* (2013.01); *A61B 5/02405* (2013.01); *A61B 5/053* (2013.01); *A61B 5/0533* (2013.01); *A61B 5/08* (2013.01); *A61B 5/16* (2013.01);
(Continued)

(58) Field of Classification Search
None
See application file for complete search history.

(56) References Cited

U.S. PATENT DOCUMENTS

| 2006/0029198 | A1* | 2/2006 | Dorneich | A61B 5/0002 379/88.22 |
| 2007/0197881 | A1 | 8/2007 | Wolf et al. | |

(Continued)

FOREIGN PATENT DOCUMENTS

WO 2014052938 4/2014

OTHER PUBLICATIONS

International Preliminary Report on Patentability (PCT/IB/326); 1 Sheet; Date of Issuance: Nov. 14, 2017 (Nov. 14, 2017); dated Nov. 23, 2017 (Nov. 23, 2017); International application No. PCT/US2016/032778.

(Continued)

*Primary Examiner* — Jason T Yen
(74) *Attorney, Agent, or Firm* — Lieberman & Brandsdorfer, LLC

(57) ABSTRACT

Embodiments of the invention relate to correlation of physiological data from two or more sources in real-time. As data is gathered from one or more remote physiological sensors, evaluation of associated physiological data takes place in real-time. The sensor data is correlated with other forms of data including objective physiological data, subjective physiological data, cognitive data, and/or quantitative input for multi-variate data analytics to assess and correlate the data. Alerts are generated, applications are activated, and windows are created to support the correlation and associated communication.

30 Claims, 7 Drawing Sheets

(51) Int. Cl.
*A61B 5/0205* (2006.01)
*A61B 5/024* (2006.01)
*A61B 5/08* (2006.01)
*A61B 5/053* (2006.01)
*A61B 5/01* (2006.01)
*A61B 5/00* (2006.01)

(52) U.S. Cl.
CPC ........... *A61B 5/4806* (2013.01); *A61B 5/7264* (2013.01); *A61B 5/7275* (2013.01); *A61B 2562/0219* (2013.01)

(56) References Cited

U.S. PATENT DOCUMENTS

| | | | |
|---|---|---|---|
| 2011/0172499 A1* | 7/2011 | Simons-Nikolova | ........................ A61B 5/0002 600/300 |
| 2012/0071731 A1* | 3/2012 | Gottesman | ........... A61B 5/6833 600/301 |
| 2012/0259803 A1* | 10/2012 | Whitlow | .................. A61B 5/16 706/20 |
| 2012/0295589 A1* | 11/2012 | Alexander | .......... H04L 63/0861 455/411 |
| 2015/0148621 A1* | 5/2015 | Sier | ...................... A61B 5/7267 600/301 |
| 2015/0182129 A1* | 7/2015 | Colley | ................. A61B 5/0205 600/301 |

OTHER PUBLICATIONS

Written Opinion of the International Searching Authority (PCT/IB/373), 5 Sheets; Date of Issuance: Nov. 17, 2016 (Nov. 17, 2016); dated Nov. 23, 2017 (Nov. 23, 2017); International application No. PCT/US2016/032778.

International Search Report (PCT/IB/210); 3 Sheets; Date of Issuance: Nov. 17, 2016 (Nov. 17, 2016); International application No. PCT/US2016/032778.

* cited by examiner

MULTI-SYMPTOM TOOLKIT FOR EVALUATING READINESS

CROSS REFERENCE TO RELATED APPLICATION(S)

This application is a non-provisional patent application claiming the benefit of the filing date of U.S. patent application Ser. No. 62/161,507 filed on May 14, 2015 and titled "Portable Automated Sensor Suite (PASS) Motion-Induced Use Symptomology Toolkit for Evaluating Readiness (MUSTER)" which is hereby incorporated by reference.

BACKGROUND

The present embodiments relate to a system for performance readiness assessment. More specifically, the embodiments support passive acquisition of physiological and non-physiological data, and correlation of the acquired data that may impact performance.

Physical performance relates to the ability to perform a physical task. Such performance may be measured with one or more sensors. For example, wearable sensors are known in the art to measure physiological parameters during or following exercise. An example measurement may be heart rate. Other forms of wearable sensors may measure distance traveled, pace, speed, etc. In general, physical performance is a function of size, shape, sex, and age. Data from these sensors can be used to measure performance factors. For example, recent commercialization of these sensors may be found in a physical activity tracker device that tracks steps, distance, calories burned, etc. Accordingly, physical performance tracking devices are known in the art.

There are limitations associated with tracking physical activity through use of a wearable tracking device. Specifically, such devices are known to track activity and inactivity, but they do not provide insight to take any intelligent action from any associated data. For example, it is understood that if the tracked data is not within defined limits, further evaluation of the subject may be warranted. In other words, if the sensor data is considered low for the subject, and an alarm is generated, this alarm is merely an audible communication platform to indicate that the data is in a low range. There is no venue for further assessment to determine when the data is in the low range. In other words, the physical activity tracker merely gathers data associated with activity, or in one embodiment, inactivity, and may even process the data to demonstrate changes in physical activity over time. However, the physical activity tracker is essentially a closed system as it merely tracks data from a select category of sensors. The physical activity tracker does not interface with components external to the sensors and associated sensor data. Accordingly, the physical activity tracker is limited to the sensor and associated sensor data, and does not provide insight or suggestions into further evaluation for improvement, or the basis for any assessed impairment.

SUMMARY

These and other features and advantages will become apparent from the following detailed description of the presently preferred embodiment(s), taken in conjunction with the accompanying drawings.

Embodiments support includes a system and computer implemented method to dynamically distribute performance data over a network to a remote subscriber computer. An assessment application is provided to a subscriber for installation on the remote subscriber computer. Sensor data is sent across a first communication channel from a data source and the data is received at the remote computer. More specifically, the remote computer is configured with a microprocessor and a memory, with the memory configured to store preferences for information format, destination address, and specified data values. The microprocessor functions to generate state data based on the sensor data. More specifically, the microprocessor functions to activate a state classification application which causes the sensor data to display on the remote computer. The state classification application generates first state data from the sensor data, with the first state data characterizing the sensor data. In addition, the first state data activates a cognitive assessment module in a secondary window. The cognitive assessment module evaluates a cognitive state and generates cognitive state data from the evaluated cognitive state.

BRIEF DESCRIPTION OF THE SEVERAL VIEWS OF THE DRAWINGS

The drawings referenced herein form a part of the specification. Features shown in the drawings are meant as illustrative of only some embodiments, and not of all embodiments unless otherwise explicitly indicated.

DETAILED DESCRIPTION

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

Figure 1:
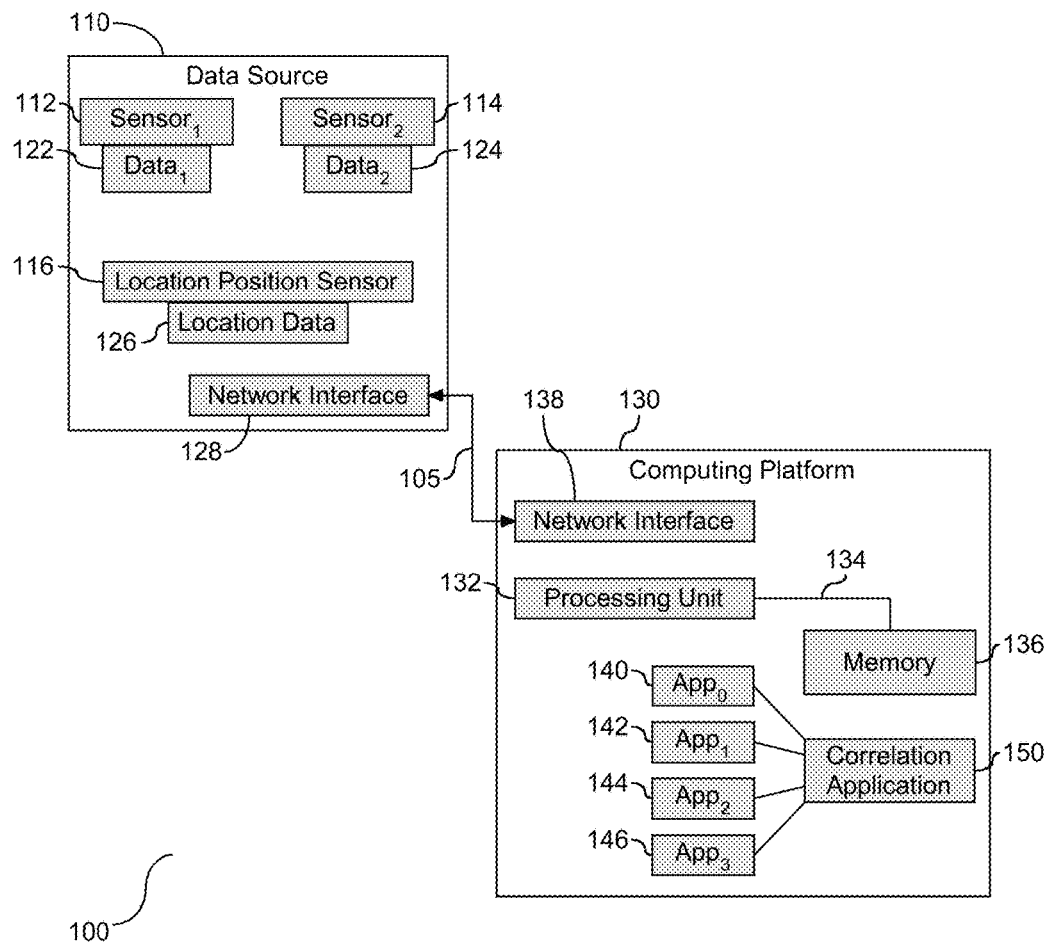
FIG. 1 depicts a block diagram illustrating a system and associated components employed for physiological and behavioral state assessment.

With reference to FIG. 1, a system (100) is provided illustrating components employed for physiological and behavioral state assessment. As shown, a data source (110) is provided in communication with a computing platform (130). More specifically, the data source (110) is shown herein with two sensors (112) and (114), a location position device (116), e.g. global position indicator, and a wireless communication interface (118). In one embodiment, the location position device (116) may be optional, and as such, should not be considered a limiting embodiment. Although two sensors (112) and (114) are shown herein, this quantity of sensors should not be considered limiting. One or both of the sensors (112) and (114) may be a physiological sensor to detect a physical property. Sensors (112) and (114) may track physiological and behavioral state data relating to sleep, activity, stress, nervous system function, etc. in real-time. A physiological sensor may be employed to track physiological parameters such as heart rate, respiration, skin conductance, or skin temperature relevant to real-time and over time physiological state sensing. For example, a heart rate sensor may track heart rate variability, a respiration sensor may track respiration, a thermistor may track skin temperature, one or more electrodes may function as a sensor to track galvanic skin response, etc. A behavioral sensor may be employed to track activities such as sleep and exercise. For example, an inertial measurement unit (IMU) may be employed to track behavioral state data in the form of movement and activity data. Various behavioral state sensors may be employed, such as an accelerometer or a gyroscope. The types of sensors should not be considered limiting. Similarly, the sensors (112) and (114) may be different, such that they acquire different categories of data. For example, in one embodiment, sensor (112) may be configured to acquire physiological data and sensor (114) may be an IMU to acquire activity and related behavior data. Although sensors (112) and (114) are shown embedded in data source (110), in one embodiment, there may be two or more data sources with one or more sensors in communication with platform (130). As such, the sensors (112) and (114) do not need to be local to the same data source. Accordingly, the sensors (112) and (114) function to gather associated data and to communicate the data to a computing platform (130).

In one embodiment, the sensor (112) is worn on the body of a subject. For example, the sensor may be embodied in a wrist band, a chest strap, as a ring on a finger, etc. Each sensor (112) and (114) generates associated sensor data (122) and (124), respectively, and global position data (126). In one embodiment, each sensor embedded in the data source (110) is configured to gather different forms and/or categories of physiological data. Accordingly, two or more sensors (112) and (114), and the global position indicator (116), are provided in communication with the data source (110) to gather associated data and to employ the network interface (118) for transmission of the data.

As shown, the wireless communication interface (118) is provided in communication with the sensors (112) and (114). The data (122) and (124) gathered from the sensors (112) and (114), respectively, and the location data (126) is communicated to the computing platform (130) across a communication channel (105). In one embodiment, the communication channel (105) is wireless. Similarly, in one embodiment, the communication channel (105) may be a uni-directional channel to support communication of data (122)-(126) from the data source (110) to the computing platform (130). In one embodiment, the communication channel (105) may be bi-directional and support communication of data from the data source (110) to the computing platform (130) and from the computing platform (130) to the data source (110).

The data (122)-(126) may be communicated to the computing platform (130) via streaming, on a periodic basis or on-demand. In one embodiment, the frequency of transmission of the data (122)-(126) may be customarily configured. Similarly, in one embodiment, the frequency may be automatically adjusted by an application in communication with the data source (110), as will be described in detail below. In one embodiment, the data source (110) and the platform (130) may employ Bluetooth pairing for communication across the communication channel (105), although other forms of wireless communication may be supported, and as such, the communication protocol should not be considered limiting. Accordingly, the data source (110) is configured to accumulate and transmit data (122)-(126) from the data source (110) to the computing platform (130).

As shown herein, the computing platform (130) is configured with a processing unit (132), or in one embodiment, a microprocessor, in communication with memory (136) across a bus (134). The platform (130) is further provided with a network interface (138) to support wired or wireless communication with the data source (110). The computing platform (130) may be in the form of a personal computer, a tablet, or a mobile telecommunication device. The platform (130) is shown configured with a plurality of applications to support assessment and correlation of data (122)-(126). In one embodiment, preferences for information format and a destination address are stored in memory (136). Similarly, in one embodiment, specified physiological and behavioral data values are stored in memory. Four applications are shown herein, including $APP_0$ (140), $APP_1$ (142), $APP_2$ (144), and $APP_3$ (146). Each application gathers and/or processes data associated with the functionality of the application. In one embodiment, one or more of the applications (140)-(146) employs data (122)-(126). Accordingly, each application is supported by the processor (132) for execution of associated instructions supporting the functionality of the application.

At least one of the applications (140)-(146) supports cognitive assessment and/or cognitive data. As shown herein, $APP_0$ (140) is designated as supporting the cognitive assessment and/or cognitive data. The remaining applications shown pertain to physiological and behavioral assessment and data input. In one embodiment, sensors (112) and (114) are different categories of sensors and acquire different types of data, with each data type being supported by a different application or a single application. For example, $APP_1$ (142) is shown in communication with sensors (112) and (114) and functions to process the associated data (122) and (124). In one embodiment, a separate application (not shown) may be provided in communication with sensor (114) and function to process data (124) so that sensor data (122) and (124) are separately processed. In one embodiment, a single application, such as $APP_1$ (142) may employ aspects of data (122) and (124). $APP_2$ (144) is an application that supports subjective input pertaining to physiological and behavioral data. For example, $APP_2$ (144) may present a platform to a subject to obtain direct feedback. In one embodiment, $APP_2$ (144) quantifies subjective data received from the subject. Examples of the subjective data may include, but is not limited to, scales of sleepiness, stress, mood, activity, etc. In one embodiment, $APP_2$ (144) provides a portal for gathering the associated subjective data. APP$_3$ (146) is an application that supports quantitative input, such as but not limited to, quantitative information regarding sleep, nutrition, and activity. Details of application data processing are shown and described below in FIGS. 3 and 4. In addition, to applications (140)-(146), a correlation application (150) is provided in communication with applications (140)-(146). The correlation application (150) functions to combine different categories of state data. In one embodiment, application (150) correlates data output from the respective applications (140)-(146). Details of the functionality of the correlation application (150) are described in detail in FIGS. 3 and 4.

Figure 2:
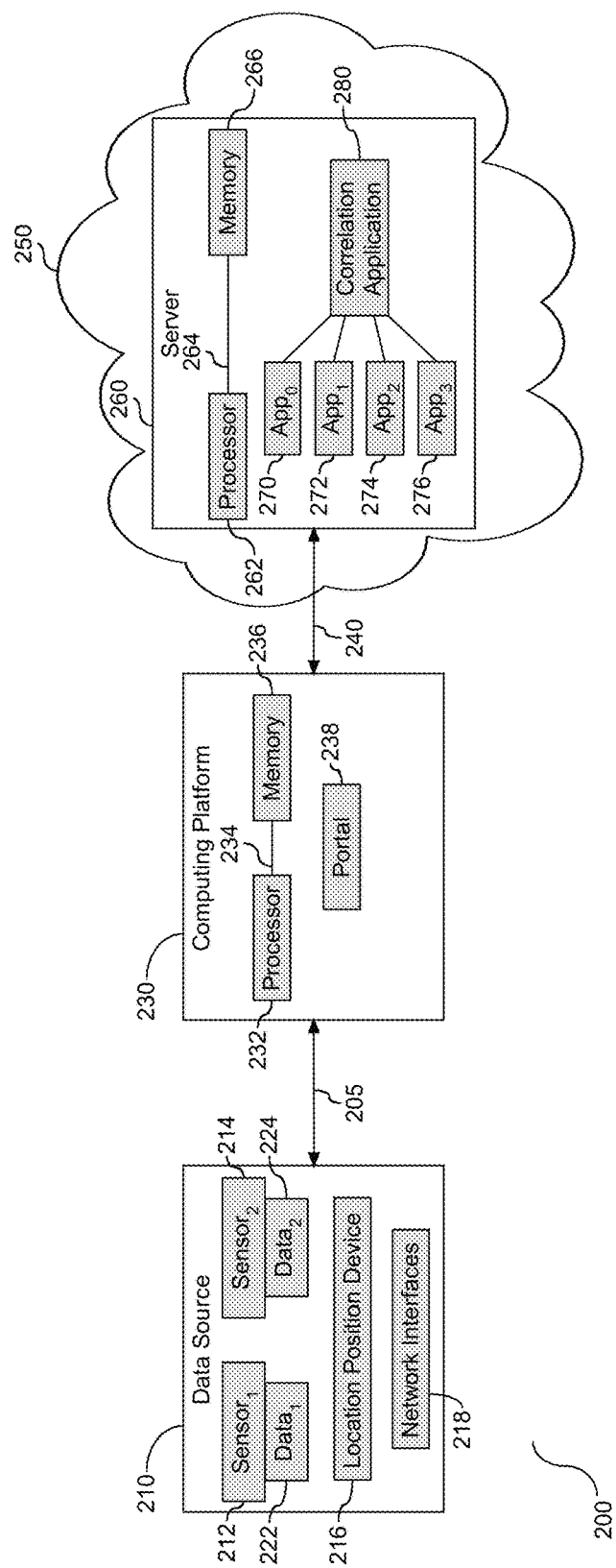
FIG. 2 depicts a block diagram illustrating system and associated components for physiological and behavioral state assessment in a shared resource environment.

Referring to FIG. 2, a system (200) is provided illustrating components employed for physiological and behavioral state assessment in a shared resource environment. Similar to the system shown and described in FIG. 1, a data source (210) is provided in communication with a computing platform (230). More specifically, the data source (210) is shown herein with two sensors (212) and (214), location position device (216), e.g. GPS location device, and a wireless communication interface (218). The functionality of the sensors (212) and (214) and the location position device (216) are parallel to sensors (112) and (114) and location position device (116) shown and described in FIG. 1, and are hereby incorporated by reference.

As shown, the wireless communication interface (218) is provided in communication with the sensors (212) and (214) and the location position device (216). The data (222) and (224), also referred to as performance data, gathered from the sensors (212) and (214), respectively, and location data (226) gathered from the location position device (216) is communicated to the computing platform (230) across a first communication channel (205). In one embodiment, the communication channel (205) is wireless. Similarly, in one embodiment, the communication channel (205) may be a uni-directional channel to support communication of data (222)-(226) from the data source (210) to the computing platform (230). In one embodiment, the communication channel (205) may be bi-directional and support receipt of data from the computing platform (230).

The data (222)-(226) may be communicated to the computing platform (230) via streaming, on a periodic basis or on-demand. In one embodiment, the frequency of transmission of the data may be customarily configured. Similarly, in one embodiment, the frequency may be automatically adjusted by an application in communication with the data source (210), as will be described in detail below. In one embodiment, the data source (210) and the computing platform (230) may employ Bluetooth pairing for communication, although other forms of wireless communication may be supported, and as such, the communication protocol should not be considered limiting. Accordingly, the data source (210) is configured to accumulate and transmit data (222)-(226) from the data source (210) to the computing platform (230).

As shown herein, the computing platform (230) is configured with a processing unit (232) in communication with memory (236) across a bus (234). The computing platform (230) may be in the form of a personal computer, a tablet, or a mobile telecommunication device. The platform (230) is shown in communication with a shared computing resource(s) (250) across a second communication channel (240). See FIGS. 4-6 for further description of the resource(s). The computing platform (230) is configured with a portal (238) that functions to manage receipt and initial processing of the data (222)-(226).

Assessment and correlation of the data (222)-(226) is provided in the shared computing environment (250). More specifically, the environment (250) is shown with a server (260) with a processing unit (262) in communication with memory (266) across a bus (264). The server (260) is shown configured with a plurality of applications to support evaluation and correlation of performance data, including physiological and behavioral assessment as well as quantitative and subjective data. Four applications are shown herein, including APP$_0$ (270), APP$_1$ (272), APP$_2$ (274), and APP$_3$ (276). Each application gathers and/or processes data associated with the functionality of the application. In one embodiment, the environment is configured with more than one server, with the applications located on different servers in the environment.

At least one of the applications supports cognitive assessment and/or cognitive data. As shown herein, APP$_0$ (270) is designated as supporting the cognitive assessment and/or cognitive data. The remaining applications shown pertain to physiological assessment as well as assessment of data pertaining to quantitative and subjective input. For example, APP$_1$ (272) is in remote communication with sensor (212) and/or sensor (214) across one or more communication channels (205) and/or (240). APP$_1$ (272) functions to process the associated sensor data, including data (222), and in one embodiment data (224). APP$_2$ (274) is an application that supports subjective input pertaining to physiological and behavioral characteristics. For example, APP$_2$ (274) may present a platform to a subject to obtain direct feedback. In one embodiment, APP$_2$ (274) gathers subjective data from the subject. Examples of the subjective data may include, but is not limited to, scales of sleepiness, stress, mood, activity, etc. In one embodiment, APP$_2$ (274) provides a portal for gathering the associated subjective physiological and behavioral data. APP$_3$ (276) is an application that supports quantitative input, such as but not limited to, quantitative information regarding sleep, nutrition, and activity. Details of the application data processing are shown and described below in FIG. 3. In addition, to applications (270)-(276), a correlation application (280) is provided in communication with applications (270)-(276). The correlation application (280) functions to coordinate activation and employment of the applications (270)-(276). Details of the functionality of the correlation application are described in detail in FIG. 3. Accordingly, the platform (230) and the associated portal (238) functions in conjunction with the shared computing environment (250) and the sensors of the data source (210).

Figure 3:
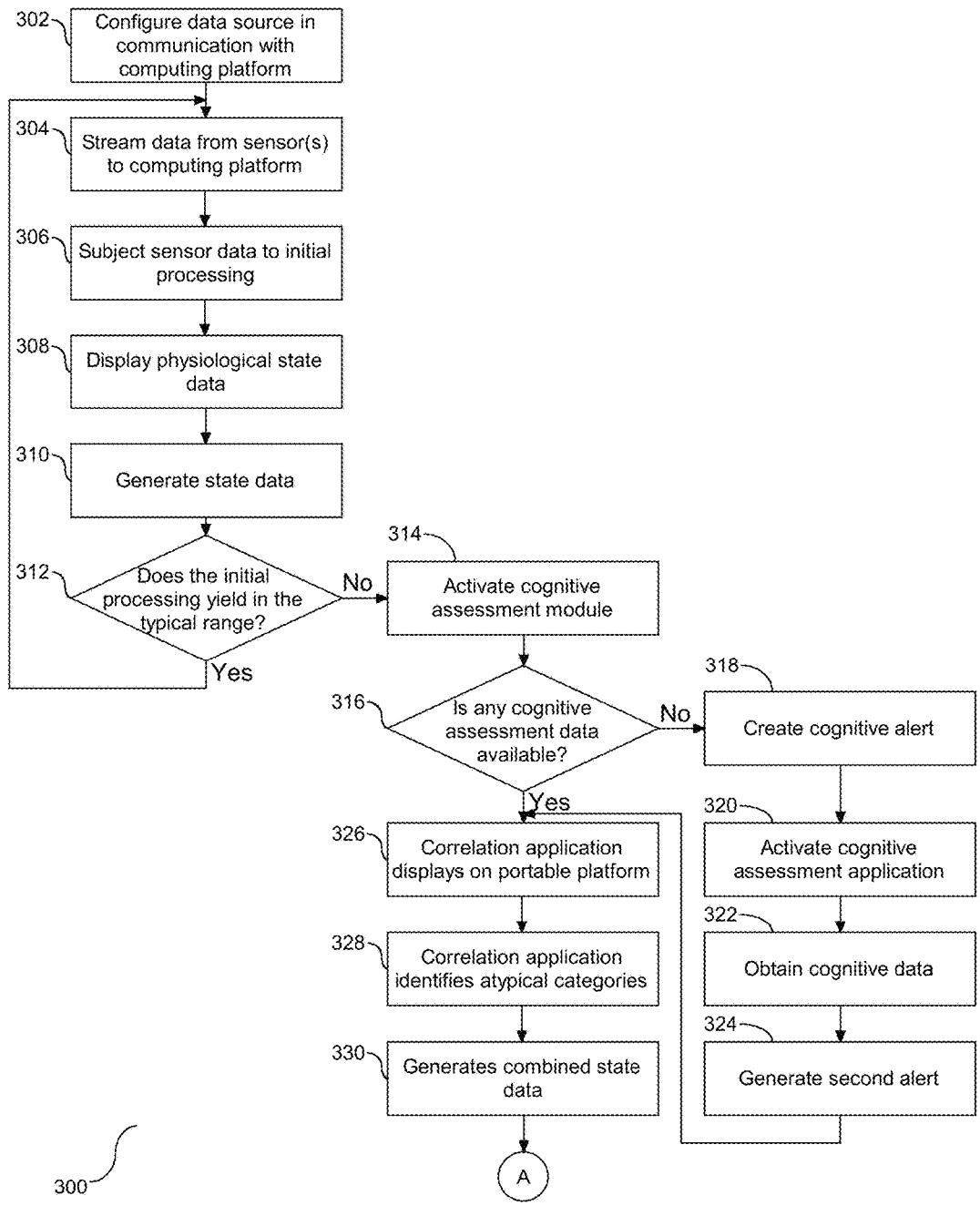
FIG. 3 depicts flow chart illustrating functionality of the data source in conjunction with the gathered sensor data.
Figure 3:
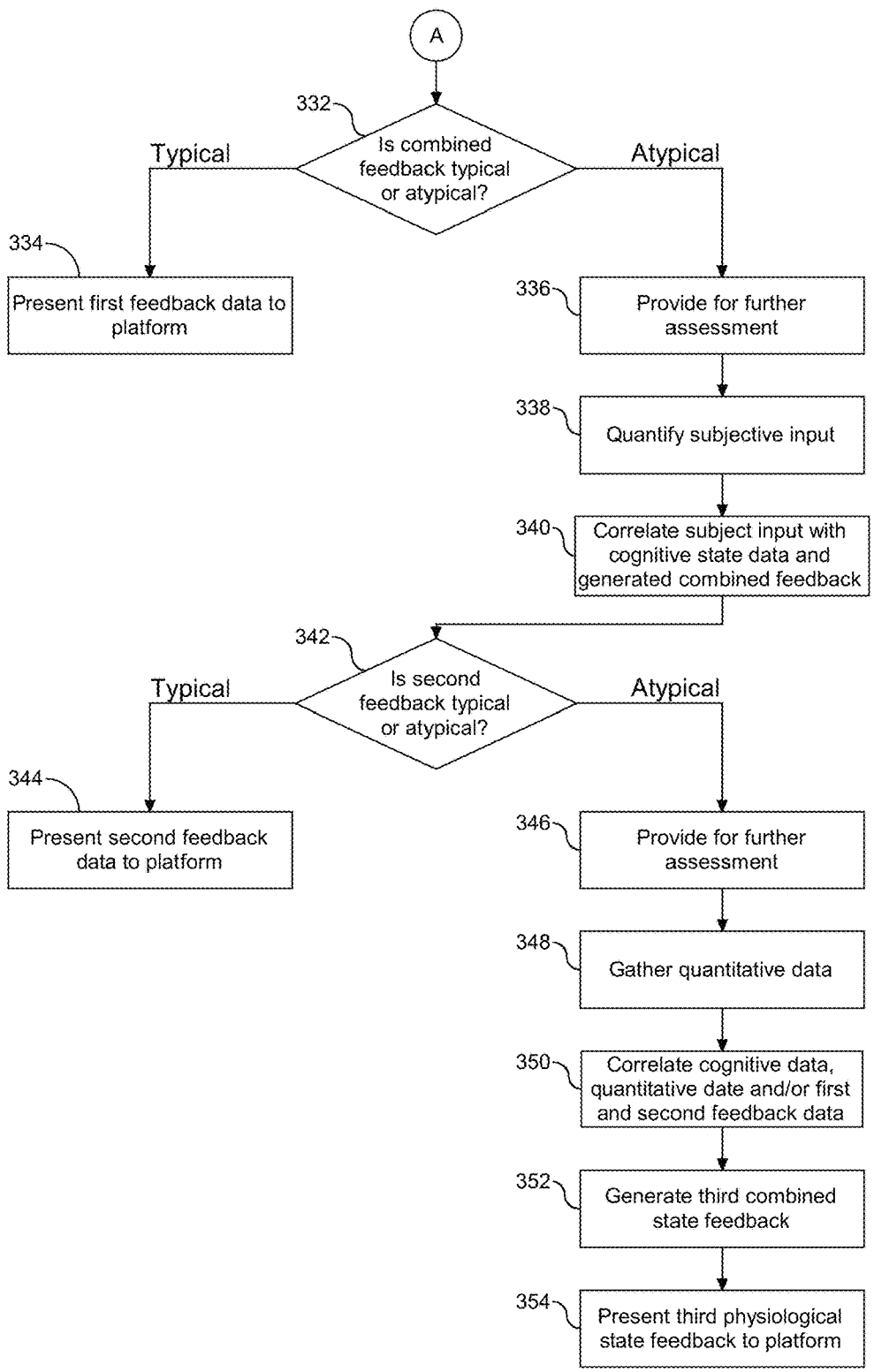

Referring to FIG. 3, a flow chart (300) is provided illustrating the functionality of the data source in conjunction with the gathered sensor data. As shown, the data source is configured with one or more physiological sensors and quantitative sensors, and the data source is configured in communication with a computing platform (302). In one embodiment, the sensors are employed to measure physical activity. As described above, the computing platform may be a portable platform such as a tablet or mobile telecommunication device. Data acquired from the sensors is stream to the computing platform (304). In one embodiment, memory local to the computing platform stores preferences for information format, destination address, and specified data values. The streaming may take place on-demand or on a periodic basis. In one embodiment, the frequency of data streaming may be adjusted. The physiological sensors gather physiological data. In one embodiment, one or more of the sensors are worn on the body of the subject, and may be in a form such as a wrist band, a chest strap, a ring on a finger, etc. In one embodiment, one or more of the sensors track sleep, activity, stress, and/or nervous system function. For example, in one embodiment, one or more of the sensors may include an inertial measurement unit for actigraphy. Other sensors may be employed to measure heart rate variability, respiration, galvanic skin response, skin temperature, etc. Similarly, in one embodiment, the physiological sensor may be customizable to gather a specific form of the physiological data. Accordingly, once the data source is configured in communication with the platform, associated physiological and/or performance data is communicated to the platform across a wireless communication protocol.

The physiological sensors acquire data, which is then subject to an initial processing (306). In one embodiment, the initial processing may include a characterization of sensor location position data. Similarly, in one embodiment, the initial processing activates and employs a state classification application, which enables or otherwise causes the sensor data to be presented on an associated visual display (308). In one embodiment, the initial processing, which is also referred to herein as filtering, takes place local to the platform, although this should not be considered a limiting embodiment. For example, in one embodiment, the initial processing may take place local to the data source, or at a different location. The initial processing at step (306) assesses the sensor data with respect to a baseline and/or range. In one embodiment, when the communication between the data source and the platform is established, the settings are calibrated. More specifically, the calibration establishes baseline and range values for the data to be acquired and communicated. In one embodiment, a profile is created from the baseline range value, which in one embodiment may be dynamically modified based on feedback. In one embodiment, the sensor is a physiological sensor, and the initial process at step (306) generates physiological state data. Based on the processing at step (306), state data characterizing the received sensor data is generated (310). In one embodiment, different subjects may have different characteristics yielding different state characterizations. For examples, different in age, height, and/or weight may contribute to the characterization. Accordingly, the initial performance assessment pertains to an initial characterization of the data.

Following the initial characterization, it is determined if an initial assessment of the sensor data is within a range defined as typical (312). In one embodiment, the processing at step (308) may detect and/or identify a trend in the data. In one embodiment, the initial assessment may be inverted with respect to an atypical range, e.g. physiological impairment. The initial assessment, and more specifically, transmission of feedback associated with the initial assessment create an alert condition which is transmitted in real-time across a communication channel to the computing platform. A positive response to the initial assessment is followed by a return to step (304) for continued streaming of the sensor data to the computing platform. In one embodiment, the frequency of the data streaming is established during calibration, although the frequency may be subject to modification. Accordingly, an initial processing of the sensor data establishes if the raw data is typical or atypical as defined with the sensor calibration, or in one embodiment determines if a trend associated with the data is present.

A negative response to the determination at step (312) is an indication that the generated state data may be atypical for the subject. More specifically, the negative response activates a cognitive assessment module (314). In one embodiment, the cognitive assessment module is activated in a secondary window of an associated visual display. The cognitive assessment module functions to evaluate a cognitive state and generate cognitive state data from the evaluation. In one embodiment, the cognitive assessment module functions from previously acquired cognitive data. Similarly, in one embodiment, previously acquired cognitive data may either not be present or it may be aged.

Following step (314), it is determined if there is any cognitive assessment data available for the subject from a prior assessment (316), or if there is cognitive assessment data available, it is determined if the data is current. In one embodiment, the subject may have previously been presented with a cognitive assessment, and as such, cognitive assessment data may be available for correlation with the acquired sensor data. A negative response to the determination at step (316) creates a first alert, also referred to herein as an alert condition, associated with cognitive assessment (318). In one embodiment, a cognitive assessment tool is embedded or integrated into the portable platform. Similarly, in one embodiment, preferences established during calibration result in transmission of the first alert from the portable platform over a data channel to the data source, which in one embodiment is a wireless device. The first alert then causes the cognitive assessment application to display on the portable platform, and in one embodiment, enables a connection from the portable platform to the data source over the Internet (320). In one embodiment, the cognitive assessment application resides in a hibernate or sleep mode, with the act of transmitting the first alert over the wireless communication channel functioning to activate the cognitive assessment application. In one embodiment, the cognitive assessment application may be embedded on a shared resource, with the first alert providing a link to between the portable platform and the shared resource, with selection of the link activating the cognitive assessment application. Similarly, in one embodiment, the a portal to the cognitive assessment application may be provided in the portable platform with the processing of associated cognitive data taking place on a shared computing resource accessible across a network connection, e.g. a cloud based resource. Accordingly, the first alert functions to activate the cognitive assessment application.

Activation of the cognitive assessment application supports obtaining current cognitive data from the subject (322). In one embodiment, the act of activating the cognitive assessment application creates, or in one embodiment activates, a window on a visual display associated with the computing platform. For example, in one embodiment, physiological assessment data may be active and present in a first window of the visual display, and the first alert automatically creates a window on the visual display for presentation of associated cognitive assessment criteria. In one embodiment, the second window is configured in a manner that does not overlap with the first window. In another embodiment, there may be an overlap of the first and second windows, but in a manner that mitigates obstruction of indicia associated with both the cognitive assessment and data acquired from the physiological assessment, or in one embodiment any acquired non-cognitive data. Accordingly, the first alert is generated based on atypical physiological data, with the alert functioning to activate a cognitive assessment tool.

The cognitive assessment application, also referred to herein as a cognitive assessment module, generates cognitive assessment data for the subject. More specifically, the cognitive assessment module includes a plurality of computer-based cognitive test batteries to evaluate cognitive impairment and generate cognitive state data from filtered cognitive data. In one embodiment, processing of the cognitive assessment data generated by the cognitive assessment application yields an indication of is typical or atypical. Similarly, in one embodiment, an initial cognitive assessment battery in the cognitive assessment module is selected based on a profile of the physiological impairment, which in one embodiment originates from the initial physiological state data. Similarly, in one embodiment, an initial cognitive assessment battery in the cognitive assessment module is selected based on the first state data or a profile of a characterization of the first state data. As shown herein, completion of the cognitive assessment generates a second alert (324) associated with a correlation application. In one embodiment, the correlation application is a tool embedded or integrated into the portable platform. Similarly, in one embodiment, preferences established during calibration results in transmission of the second alert from the portable platform over a data channel to the data source, which in one embodiment is a wireless device. Accordingly, the second alert then causes the correlation application to display on the portable platform, and in one embodiment, enables a connection from the portable platform to the data source over the Internet (326).

In one embodiment, the correlation application resides in a hibernate or sleep mode, with the act of transmitting the second alert over the wireless communication channel functioning to activate the correlation application. In one embodiment, the correlation application may be embedded on a shared resource, with the second alert providing a link to between the portable platform and the shared resource, with selection of the link activating the correlation application. Similarly, in one embodiment, a portal to the correlation application may be provided in the portable platform with the processing of associated data taking place on a shared computing resource accessible across a network connection, e.g. a cloud based resource. Accordingly, the second alert functions to activate the correlation application.

As described above, the correlation application may reside in a hibernate state of sleep mode until such time as it is transitions from this state. For example, in one embodiment, receipt of atypical data from one or more of the physiological sensors, including but not limited to physiological data, behavioral data, activity data, and quantitative and subjective data, may generate an alert to the subject, and at the same time activate the correlation application from the hibernate state. The alert to the subject may come in different forms. For example, in one embodiment, the alert may be in the form of tactile feedback across a communication channel to the sensor. Similarly, in one embodiment, the alert may be audible or visual. The alert may be communicated to a third party across the same or different communication channel. In response to the alert and transition of the correlation application to an active state, the correlation application may enable the subject or associated administrator to selectively activate or execute the available applications, including cognitive assessment, quantitative input, and subjective data. Quantitative input may include, but is not limited to, accelerometer data, etc. Subjective input may include, but is not limited to, data associated with mood, stress level, activity, etc. Similarly, in one embodiment, the correlation application may employ current data values or past data values. In one embodiment, the correlation application may be configured to employ data over a defined period, such as hours, days, weeks, months, etc.

The correlation application functions as a platform to combine multiple measurements. As shown and described in FIGS. 1 and 2, the system is configured with multiple applications referred to as $APP_0$ (140)/(240), $APP_1$ (142)/(242), $APP_2$ (144)/(244), and $APP_3$ (146)/(246). Each of these applications is provided in communication with the correlation application. The correlation application is activated following a positive response to the determination at step (316), so that the correlation application may utilize current cognitive assessment data, or the application may be activated following step (324) with data obtained from a current cognitive assessment. Upon activation, the correlation application identifies one or more categories of data that are atypical (328), or in one embodiment, detect trends within or across data sources. It is understood that the physiological and/or performance data from the data source, as well as data associated with behavior and activity that is either subjective or quantitative, will have at least one category of data that indicates atypical, and in one embodiment, at least one category within the cognitive assessment data may indicate as atypical. Accordingly, the atypical assessment at step (328) may be based solely on the cognitive data, solely on the data acquired from the data source, or a combination of the cognitive and acquired data.

Following the identification at step (328), the correlation application evaluates cognitive data from the cognitive assessment with identified data from the sensor(s) (330). The evaluation at step (330) generates feedback associated with physiology, behavior, and activity, that is either quantitative or subjective, referred to herein as a combined feedback, that specifies a combined state (330). Namely, the combined state is based on evaluation and correlation of one or more categories of the cognitive assessment data within one or more categories of the generated state data. This combined feedback data is assessed to determine if it is typical or atypical (332). At such time as communication between the data source and the platform is established, settings are calibrated, which in one embodiment may include values for typical and atypical data from the combined feedback. In one embodiment, the values may be subject to change. Accordingly, the correlation application is employed to bring together sensor data with cognitive assessment in the form of feedback.

It is understood that there are different tools to gather different forms of physiological data. As shown herein, a sensor is employed to gather non-subjective physiological data. There are also tools to gather subjective data relevant to physiological state. As shown herein, the assessment at step (332) may produce state data that is indicates a typical or atypical state, or in one embodiment indicates that a trend has been detected. A response at step (332) indicative that the first state data is typical, and as shown herein is followed by presenting the combined feedback to the computing platform (334). In one embodiment, receipt of the data by the platform may be followed by generation of an alert and/or presentation of the combined feedback data in a separate window on an associated visual display. In one embodiment, combined feedback may be presented in response to an atypical finding at step (336). Similarly, in one embodiment, the combined feedback, whether typical or atypical, may be transmitted to the data source. The feedback may be visual, auditory, and/or tactile. The functionality of the alert and or separate window is similar to that shown and described with activation of the cognitive assessment tool.

A response to the determination at step (332) that the first feedback data is atypical, e.g. yields results in an atypical range, is followed by providing an opportunity to further assess the subject (336). Accordingly, the combined feedback enables further assessment and insight as to the source of the atypical data.

A subjective application is provided as a platform to gather subject input from the subject. More specifically, the platform poses questions to the subject to validate or otherwise quantify physiological and behavioral characteristics (338). Examples of the subjective input may include, but is not limited to, momentary scales of sleepiness, fatigue, stress, mood, and activity. Other forms of gathering subjective physiological and behavioral characteristics may be employed through the platform, and as such, the examples shown and described herein should not be considered limiting. When the subject has completed the manual assessment, the correlation application evaluates the cognitive data with subjective input (340). The evaluation at step (340) generates a combined feedback that specifies a physiological or behavioral state data referred to herein as a second combined state. Namely, the second combined state is based on evaluation and correlation of one or more categories of the cognitive assessment data within one or more categories of the physiological data received from the subjective feedback. In one embodiment, the correlation at step (340) may include physiological state data received from the physiological sensor data. Accordingly, the second combined state data includes data received from the subjective input platform.

This second feedback data is assessed to determine if it is typical or atypical (342). At such time as communication between the data source and the platform is established, settings are calibrated, which in one embodiment may include values for typical and atypical data from the second feedback data. In one embodiment, the values may be subject to change. Accordingly, the correlation application is employed to bring together subjective physiological data with cognitive assessment and/or objective physiological sensor data in the form of second state assessment feedback.

A response at step (342) that is an indication within the typical range is followed by presenting the second combined state to the computing platform (344). In one embodiment, receipt of the data by the platform may be followed by generation of an alert and/or presentation of the second feedback data in a separate window on an associated visual display. Similarly, in one embodiment, the alert may include a communication across a channel from the platform to the data source, with the alert being tactile, audible, visible, or combinations thereof. The functionality of the alert and or separate window is similar to that shown and described with activation of the cognitive assessment tool. The response to the determination at step (342) may indicate that the second combined state yields results in an atypical range, which may provide an opportunity to further assess the subject (346). Accordingly, the second combined feedback enables further assessment and insight as to the source of the atypical finding.

It is understood that in addition to sensor to gather the physiological feedback data, sensors may be employed to gather other forms of quantitative data from the subject. Examples of such data include data pertaining to sleep, nutrition, and activity. Following step (346), the correlation application is employed to gather forms of quantitative data (348), if such data is available. In one embodiment, the correlation application activates a window on the computing platform to gather the quantitative data. Based on the availability of this quantitative data, the correlation application evaluates the current cognitive assessment data with the quantitative data (350) and generates a combined feedback that specifies a combined state (352). In one embodiment, the correlation at step (350) may include the quantified subjective data from step (340) and/or the first state data associated with the sensors. Similarly, in one embodiment, the correlation at step (350) may include a correlation of a combination of data to the cognitive test data, including any combination of physiological, behavioral, subjective and quantitative data. In one embodiment, the employment of the first and second feedback data is optional. Similarly, in one embodiment, the evaluation of the quantitative feedback data may take place prior to the subjective input data that generates the second feedback data. The evaluation at step (350) generates physiological state data referred to herein as a third physiological state assessment feedback (352). Namely, the third feedback is based on evaluation and correlation of one or more categories of the cognitive assessment data within one or more categories of the physiological data received from the data sensors. This third feedback data is presented on the visual display (354). Accordingly, the correlation application is employed to bring together physiological sensor data with cognitive assessment and quantitative data in the form of state assessment feedback.

As shown and described in FIG. 3, atypical results enables the correlation application to activate secondary assessment tools to correlate data from one or more applications. In one embodiment, the subject of the assessment or an administrator of the assessment may assert and activate a secondary assessment tool in response to atypical results, or in one embodiment in response to typical results. Similarly, in one embodiment, the correlation application may select to exclude cognitive assessment data from the evaluation, and strictly employ the physiological sensor data and/or other forms of quantitative and/or subjective physiological data.

As shown and demonstrated herein, sensors in the form of physiological sensors and/or non-physiological sensors are configured in communication with a subject and in wireless communication with a computing platform. At the same time, the correlation application functions as a platform to receive the data, assess the data, and activate alerts to gather additional data, if warranted. The correlation application functions as a platform to gather the sensor data, and also to support receipt of manual data from the subject. Accordingly, the correlation application and platform uses multivariate data analytics to assess and correlate data from multiple sources.

As shown and described with reference to FIGS. 1-3, the correlation platform functions to bring together various forms of data for both typical and atypical findings. More specifically, the correlation platform enables coordination between different environments, together with wireless communication with sensors. A computing platform is shown and described to support the correlation platform. In one embodiment, the computing platform may be supported by a service provider of a cloud computing environment, or other shared pool of configurable computer resources. For example, in one embodiment, the applications that communicate with the correlation platform, or even the correlation platform on its own, may be accessible in the cloud as a shared resource. In one embodiment, the cloud computing environment may function as a portal for activating specific applications, and/or processing associated data. For example, the correlation platform may be available on a subscription basis with different levels of subscription enabling different levels of functionality. The subscriber implementation may make the correlation platform accessible via a network connection, or in one embodiment may support installation of a portal or application on a remote subscriber application.

Figure 4:
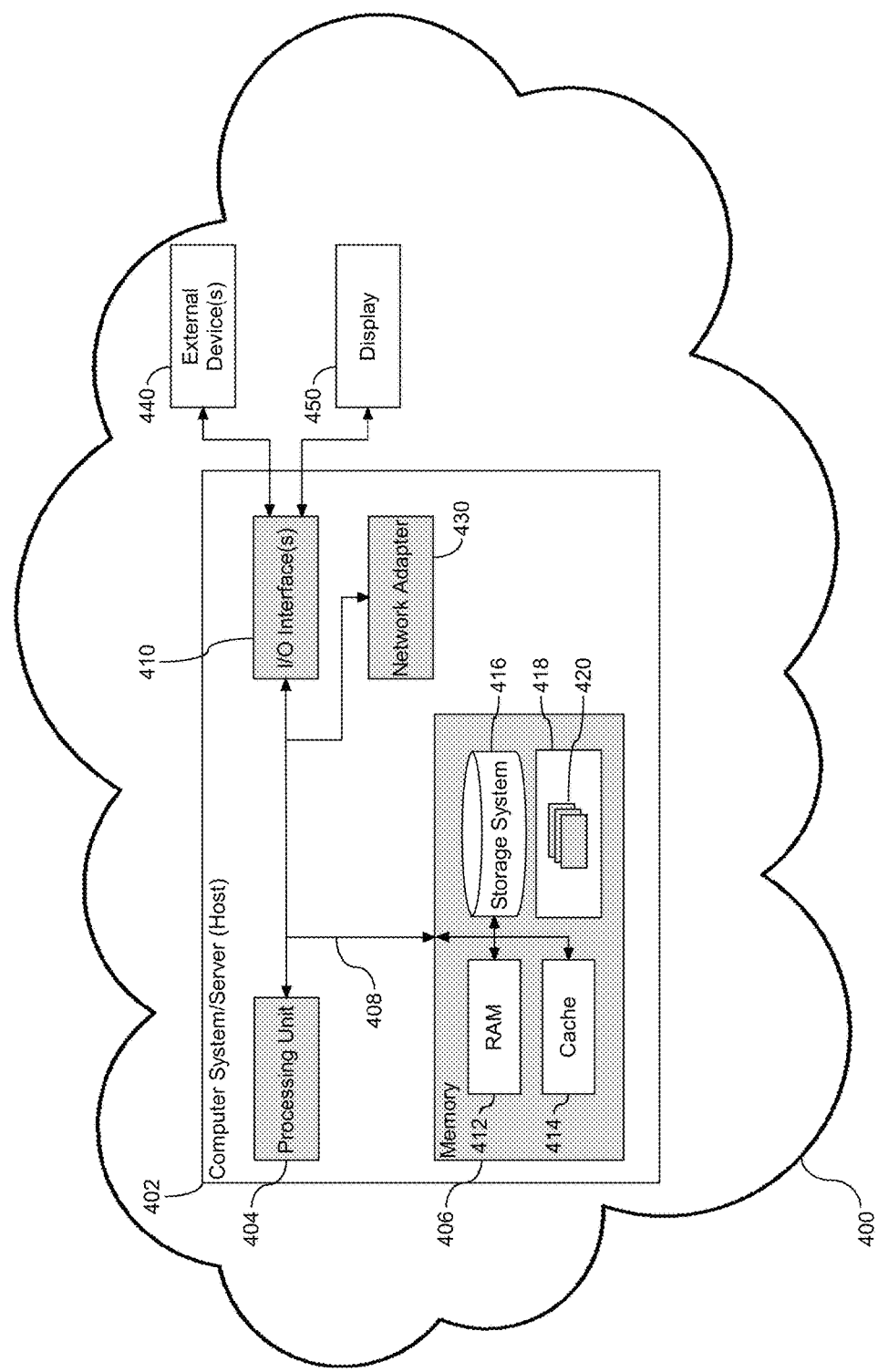
FIG. 4 depicts a block diagram illustrating an example of a computer system to implement the process of FIG. 3 and the system of FIGS. 1 and 2.

With reference to FIG. 4, a block diagram (400) is provided illustrating an example of a computer system/server (402), hereinafter referred to as a host (402) of a cloud based support system, to implement the processes described above with respect to FIGS. 1-3. Host (402) is operational with numerous other general purpose or special purpose computing system environments or configurations. Examples of well-known computing systems, environments, and/or configurations that may be suitable for use with host (402) include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and file systems (e.g., distributed storage environments and distributed cloud computing environments) that include any of the above systems or devices, and the like.

Host (402) may be described in the general context of computer system-executable instructions, such as program modules, being executed by a computer system. Generally, program modules may include routines, programs, objects, components, logic, data structures, and so on that perform particular tasks or implement particular abstract data types. Host (402) may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, host (402) is shown in the form of a general-purpose computing device. The components of host (402) may include, but are not limited to, one or more processors or processing units (404), a system memory (406), and a bus (408) that couples various system components including system memory (406) to processor (404). Bus (408) represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Host (402) typically includes a variety of computer system readable media. Such media may be any available media that is accessible by host (402) and it includes both volatile and non-volatile media, removable and non-removable media.

Memory (406) can include computer system readable media in the form of volatile memory, such as random access memory (RAM) (412) and/or cache memory (414). Host (402) further includes other removable/non-removable, volatile/non-volatile computer system storage media. By way of example only, storage system (416) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus (408) by one or more data media interfaces.

Program/utility (418), having a set (at least one) of program modules (420), may be stored in memory (406) by way of example, and not limitation, as well as an operating system, one or more application programs, other program modules, and program data. Each of the operating systems, one or more application programs, other program modules, and program data or some combination thereof, may include an implementation of a networking environment. Program modules (420) generally carry out the functions and/or methodologies of embodiments of disaster recovery as described herein. For example, the set of program modules (320) may include the correlation application and/or the applications that are configured to support the correlation application to implement the integration or physiological and cognitive assessment and recovery processes described above with reference to FIGS. 1-3.

Host (402) may also communicate with one or more external devices (440), such as a keyboard, a pointing device, etc.; a display (450); one or more devices that enable a user to interact with host (402); and/or any devices (e.g., network card, modem, etc.) that enable host (402) to communicate with one or more other computing devices. Such communication can occur via Input/Output (I/O) interface(s) (410). Still yet, host (402) can communicate with one or more networks such as a local area network (LAN), a general wide area network (WAN), and/or a public network (e.g., the Internet) via network adapter (430). As depicted, network adapter (430) communicates with the other components of host (402) via bus (408). In one embodiment, a plurality of nodes of a distributed file system (460) is in communication with the host (402) via the I/O interface (410) or via the network adapter (430). It should be understood that although not shown, other hardware and/or software components could be used in conjunction with host (402). Examples, include, but are not limited to: microcode, device drivers, redundant processing units, external disk drive arrays, RAID systems, tape drives, and data archival storage systems, etc.

In this document, the terms "computer program medium," "computer usable medium," and "computer readable medium" are used to generally refer to media such as main memory (406), including RAM (412), cache (414), and storage system (416), such as a removable storage drive and a hard disk installed in a hard disk drive.

Computer programs (also called computer control logic) are stored in memory (406). Computer programs may also be received via a communication interface, such as network adapter (430). Such computer programs, when run, enable the computer system to perform the features of the present invention as discussed herein. In particular, the computer programs, when run, enable the processing unit (404) to perform the features of the computer system. Accordingly, such computer programs represent controllers of the computer system.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

In one embodiment, host (402) is a node of a cloud computing environment. As is known in the art, cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Example of such characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 5:
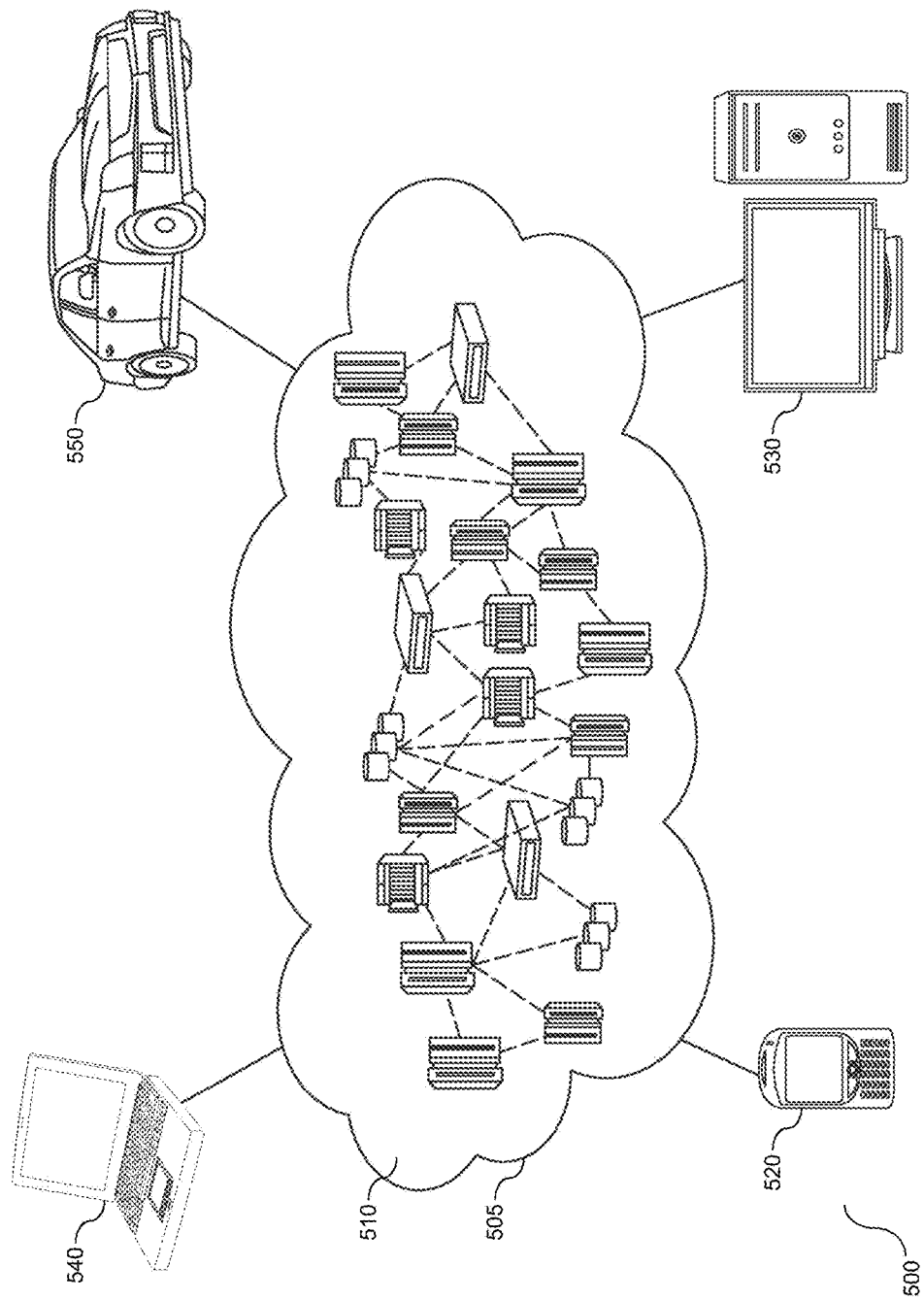
FIG. 5 depicts a block diagram of a cloud computing environment.

Referring now to FIG. 5, an illustrative cloud computing network (500). As shown, cloud computing network (500) includes a cloud computing environment (505) having one or more cloud computing nodes (510) with which local computing devices used by cloud consumers may communicate. Examples of these local computing devices include, but are not limited to, personal digital assistant (PDA) or cellular telephone (520), desktop computer (530), laptop computer (540), and/or automobile computer system (550). Individual nodes within nodes (510) may further communicate with one another. They may be grouped (not shown) physically or virtually, in one or more networks, such as Private, Community, Public, or Hybrid clouds as described hereinabove, or a combination thereof. This allows cloud computing environment (500) to offer infrastructure, platforms and/or software as services for which a cloud consumer does not need to maintain resources on a local computing device. It is understood that the types of computing devices (520)-(550) shown in FIG. 5 are intended to be illustrative only and that the cloud computing environment (505) can communicate with any type of computerized device over any type of network and/or network addressable connection (e.g., using a web browser).

Figure 6:
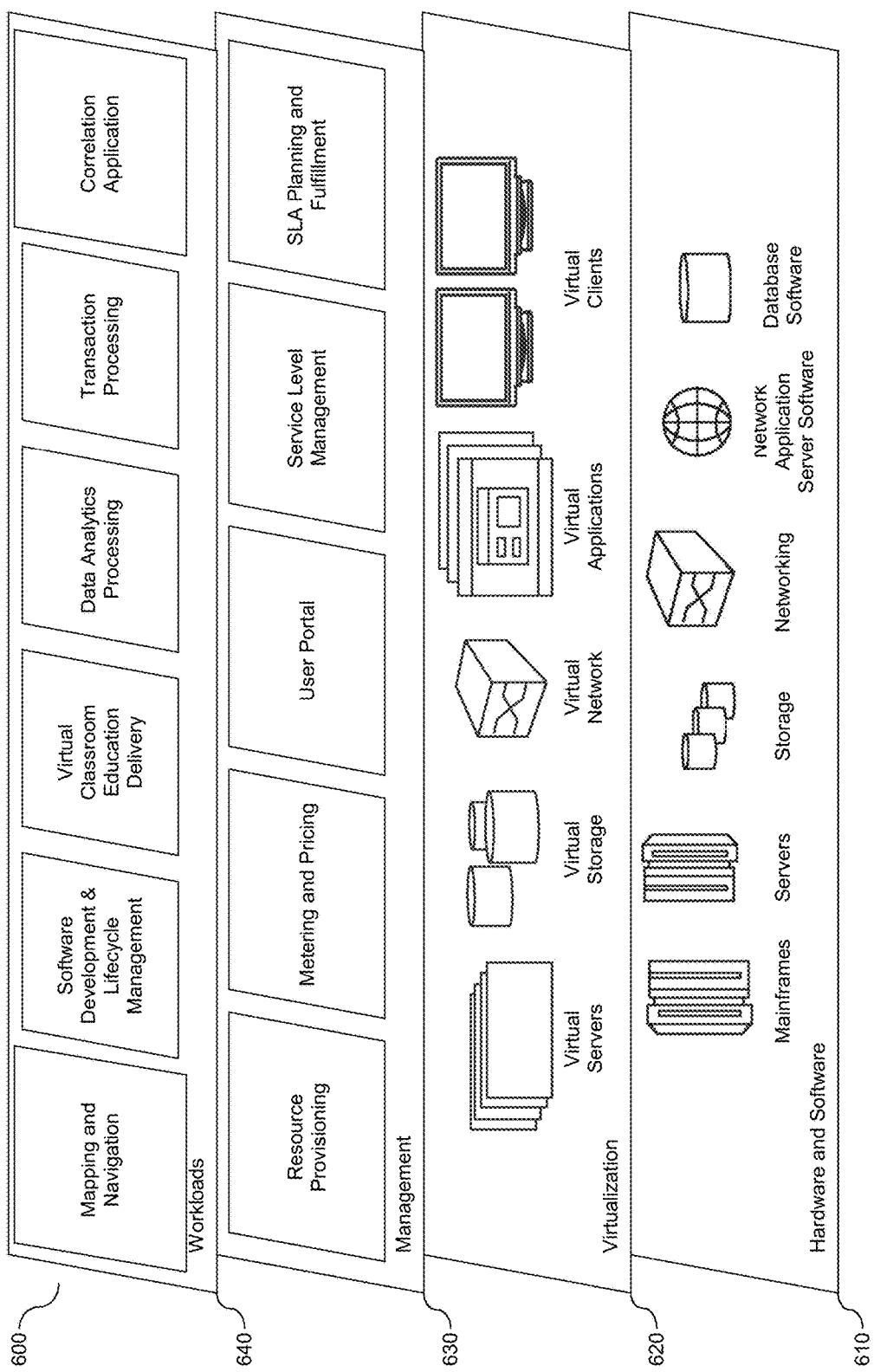
FIG. 6 depicts a block diagram illustrating a set of functional abstraction model layers provided by the cloud computing environment.

Referring now to FIG. 6, a set of functional abstraction layers provided by the cloud computing network of FIG. 5 is shown. It should be understood in advance that the components, layers, and functions shown in FIG. 6 are intended to be illustrative only, and the embodiments are not limited thereto. As depicted, the following layers and corresponding functions are provided: hardware and software layer (610), virtualization layer (620), management layer (630), and workload layer (640). The hardware and software layer (610) includes hardware and software components. Examples of hardware components include mainframes; RISC (Reduced Instruction Set Computer) architecture based servers; storage devices; networks and networking components. Examples of software components include network application server software; and database software.

Virtualization layer (620) provides an abstraction layer from which the following examples of virtual entities may be provided: virtual servers; virtual storage; virtual networks, including virtual private networks; virtual applications and operating systems; and virtual clients.

In one example, management layer (630) may provide the following functions: resource provisioning, metering and pricing, user portal, service level management, and SLA planning and fulfillment. Resource provisioning provides dynamic procurement of computing resources and other resources that are utilized to perform tasks within the cloud computing environment. Metering and pricing provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer (640) provides examples of functionality for which the cloud computing environment may be utilized. Examples of workloads and functions which may be provided from this layer include, but are not limited to: mapping and navigation; software development and lifecycle management; virtual classroom education delivery; data analytics processing; transaction processing; and correlation platform of physiological and cognitive assessment within the cloud computing environment.

The server described above in FIG. 1 has been labeled with tools in the form application and modules. The tools may be implemented in programmable hardware devices such as field programmable gate arrays, programmable array logic, programmable logic devices, or the like. The tools may also be implemented in software for execution by various types of processors. An identified functional unit of executable code may, for instance, comprise one or more physical or logical blocks of computer instructions which may, for instance, be organized as an object, procedure, function, or other construct. Nevertheless, the executable of the tools need not be physically located together, but may comprise disparate instructions stored in different locations which, when joined logically together, comprise the tools and achieve the stated purpose of the tool.

Indeed, executable code could be a single instruction, or many instructions, and may even be distributed over several different code segments, among different applications, and across several memory devices. Similarly, operational data may be identified and illustrated herein within the tool, and may be embodied in any suitable form and organized within any suitable type of data structure. The operational data may be collected as a single data set, or may be distributed over different locations including over different storage devices, and may exist, at least partially, as electronic signals on a system or network.

Furthermore, the described features, structures, or characteristics may be combined in any suitable manner in one or more embodiments. In the following description, numerous specific details are provided, such as examples of agents, to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. Accordingly, the implementation of sensors and the correlation platform integrates hardware and software, objective measures and subjective measures, visible and non-visible alert protocols, hibernate and sleep modes, and activation thereof, to support comprehensive assessment of a subject.

It will be appreciated that, although specific embodiments of the invention have been described herein for purposes of illustration, various modifications may be made without departing from the spirit and scope of the invention. In particular, two or more categories of physiological data may be correlated to create a combined physiological state data. More specifically, non-subjective physiological data acquired from physiological sensor may be combined with subjective physiological data to create the combined physiological state data, and employment of cognitive data or activation of cognitive assessment module is based on the combined physiological state data. Accordingly, the scope of protection of this invention is limited only by the following claims and their equivalents.

We claim:

1. A system comprising:
   a data source in wireless communication with a computing platform across a first communication channel, the data source including two or more sensors and generated sensor data;
   the computing platform comprising:
      a processor in communication with memory,
      a visual display in communication with the memory, the computing platform to receive the generated sensor data sent across the first communications channel and to dynamically assess sensor performance;
   the assessment further comprising:
      activation of a state classification application to cause the sensor data to display on the visual display and to enable connection to the data source;
      the state classification application to generate first state data from the sensor data in a first window on the visual display, wherein the first state data characterizes the sensor data; and
      the first state data to activate a cognitive assessment module in a second window on the visual display when the first state data is outside of the predetermined parameters, and the cognitive assessment module to evaluate a cognitive state and generate cognitive state data from the evaluated cognitive state, wherein the first and second windows are concurrently displayed on the visual display.

2. The system of claim 1, further comprising the assessment to select an initial cognitive test from the cognitive assessment module based on a profile of the characterized first state data.

3. The system of claim 1, further comprising the assessment to correlate the cognitive state data with the characterized first state data and generate a combined feedback that specifies a combined state.

4. The system of claim 1, further comprising the assessment to receive quantitative input at the computing platform, wherein the input quantifies data selected from the group consisting of: sleep, nutrition, activity, and combinations thereof.

5. The system of claim 4, further comprising the processor to correlate the quantitative input with the cognitive state data and generate a combined feedback that specifies a combined state.

6. The system of claim 4, further comprising the processor to correlate the quantitative input with the cognitive state data and the first state data and generate a combined feedback that specifies a combined state.

7. The system of claim 1, further comprising the assessment to receive subjective input at the remote computer, wherein the input quantifies data selected from the group consisting of: fatigue, stress, mood, and combinations thereof.

8. The system of claim 7, further comprising the processor to correlate the quantified subjective input with the cognitive state data and generate a combined feedback that specifies a combined state.

9. The system of claim 3, further comprising the correlation to generate a profile based on a defined typical data range and to dynamically modify the profile based on the data selected from the group consisting of: first state data and the cognitive state data.

10. The system of claim 1, further comprising a location positioning device embedded in the data source, and processor to characterize the location data received from the location positioning device with the sensor data.

11. The system of claim 1, further comprising the assessment to correlate the characterized first state data and quantitative input at the remote computer, wherein the input quantifies data selected from the group consisting of: sleep, nutrition, activity, and combinations thereof, and to generate a combined feedback that specifies a combined state, and join the combined state with the cognitive state data from the evaluated cognitive state.

12. The system of claim 1, wherein the sensor is selected from the group consisting of a physiological sensor and a physical activity sensor, and combinations thereof, and wherein the physiological sensor measures physiological state data and the physical activity sensor measures physical activity, and further comprising the assessment to correlate the characterized first state data and quantitative input and subjective input at the remote computer, wherein the input quantifies data selected from the group consisting of: fatigue, stress, mood, sleep, nutrition, activity, and combinations thereof, and generating a combined feedback that specifies a combined state, and join the combined state with the cognitive state data from the evaluated cognitive state.

13. A computer implemented method for dynamically distributing performance data over a network to a remote subscriber computer, the method comprising:
   providing an assessment application to a subscriber for installation on the remote subscriber computer;

receiving sensor data wirelessly transmitted from a sensor at the remote computer sent across a first communication channel from a data source, the remote computer comprising a microprocessor and a memory that stores preferences for information format, destination address, and specified data values, wherein the microprocessor:

activates a state classification application to cause the sensor data to display in a first window on the remote computer and to enable connection to the data source when the device is connected to the remote computer;

the state classification application generates first state data from the sensor data, wherein the first state data characterizes the sensor data; and the first state data activates a cognitive assessment module in a second window on the remote computer when the first state data is outside of the predetermined parameters, and the cognitive assessment module evaluates a cognitive state and generates cognitive state data from the evaluated cognitive state, wherein the first and second windows are concurrently displayed on the remote computer.

14. The method of claim 13 further comprising selecting an initial cognitive test from the cognitive assessment module based on a profile of the characterized first state data.

15. The method of claim 13, further comprising correlating the cognitive state data with the characterized first state data and generating a combined feedback that specifies a combined state.

16. The method of claim 15, further comprising transmitting the combined feedback over the first communication channel to the data source.

17. The method of claim 13, wherein the sensor is a physiological sensor, and the first state data is physiological state data.

18. The method of claim 13, wherein sensor measures physical activity, and the sensor is selected from the group consisting of: IMU, accelerometer, and gyroscope.

19. The method of claim 13, further comprising receiving quantitative input at the remote computer, wherein the input quantifies data selected from the group consisting of: sleep, nutrition, activity, and combinations thereof.

20. The method of claim 19, further comprising the microprocessor correlating the quantitative input with the cognitive state data and generating a combined feedback that specifies a combined state.

21. The method of claim 19, further comprising the microprocessor correlating the quantitative input with the cognitive state data and the first state data and generating a combined feedback that specifies a combined state.

22. The method of claim 13, further comprising receiving subjective input at the remote computer, wherein the input quantifies data selected from the group consisting of: fatigue, stress, mood, and combinations thereof.

23. The method of claim 22, further comprising the microprocessor correlating the quantified subjective input with the cognitive state data and generating a combined feedback that specifies a combined state.

24. The method of claim 15, further comprising the correlation generating a profile based on a defined typical data range and dynamically modifying the profile based on the data selected from the group consisting of: first state data and the cognitive state data.

25. The method of claim 13, further comprising a location positioning device embedded in the data source, and characterizing the location data received from the location positioning device with the sensor data.

26. The method of claim 17, wherein the sensor is a physiological sensor, the sensor to track data selected from the group consisting of: sleep, activity, stress, nervous system function, and combinations thereof.

27. The method of claim 13, further comprising constantly monitoring the sensor data received from the sensor to detect an alert condition, and transmitting feedback associated with the alert condition in real-time over a second communication channel to the data source.

28. The method of claim 13, further comprising constantly monitoring the sensor data received from the sensor to detect an alert condition, and communicating feedback associated with the alert condition in real-time, wherein the feedback is in a medium selected from the group consisting of : auditory, visual, tactile, and combinations thereof, wherein the feedback is local to the remote computer.

29. The method of claim 13, further comprising correlating the characterized first state data and quantitative input at the remote computer, wherein the input quantifies data selected from the group consisting of: sleep, nutrition, activity, and combinations thereof, and generating a combined feedback that specifies a combined state, and joining the combined state with the cognitive state data from the evaluated cognitive state.

30. The method of claim 13, wherein the sensor is selected from the group consisting of a physiological sensor and a physical activity sensor, and combinations thereof, and wherein the physiological sensor measures physiological state data and the physical activity sensor measures physical activity, and further comprising correlating the characterized first state data and quantitative input and subjective input at the remote computer, wherein the input quantifies data selected from the group consisting of: fatigue, stress, mood, sleep, nutrition, activity, and combinations thereof, and generating a combined feedback that specifies a combined state, and joining the combined state with the cognitive state data from the evaluated cognitive state.

* * * * *